United States Patent [19]

Dörpinghaus et al.

[11] Patent Number: 4,548,582
[45] Date of Patent: Oct. 22, 1985

[54] METHOD OF MAKING DENTAL PROSTHESES

[76] Inventors: Herbert Dörpinghaus, Elisabethstrasse 38, D-4970 Bad Oeynhausen 1; Gerhard Eikermann, Auf der Hude 45, D-4970 Bad Oeynhausen 2, both of Fed. Rep. of Germany

[21] Appl. No.: 610,523

[22] Filed: May 15, 1984

[51] Int. Cl.⁴ .............................................. A61C 11/00
[52] U.S. Cl. ........................................ 433/213; 433/184
[58] Field of Search ................ 433/213, 168, 169, 184

[56] References Cited

U.S. PATENT DOCUMENTS 1,498,415  6/1924  Wilk ..................................... 433/184

FOREIGN PATENT DOCUMENTS 321586  11/1929  United Kingdom ................. 433/184

*Primary Examiner*—John J. Wilson
*Attorney, Agent, or Firm*—Max Fogiel

[57] ABSTRACT

A method of making dental prosthesis in which an occlusion model representing a jaw impression obtained with the existing prosthesis is prepared, a guideline is marked a short distance from the edge of the prosthesis. A thin layer of adhesive is applied to the penciled guideline on the occlusion model to fasten a wax wire along the penciled guideline and both ends of the wire fused together. The dental prosthesis is ground to a volume at which the wax wire, when it is placed on the occlusion model, will be completely unencumbered with respect to the prosthesis. The edge of the prosthesis is refilled with a mass of plastic until the wax wire is completely embedded in it and the freshly applied mass of plastic polymerized. The prosthesis, which has been removed from the occlusion model is worked and the wax wire baked or evaporated out of it. The ring groove left when the wax wire is removed is ground out, and tissue-compatible soft sealing material inserted into the ring groove in the dental prosthesis all the way around.

5 Claims, 7 Drawing Figures

METHOD OF MAKING DENTAL PROSTHESES

BACKGROUND OF THE INVENTION

The present invention relates to a method of making dental prostheses for the upper or lower jaw in accordance with their individual design.

All previously known measures for ensuring the adhesion of dental prostheses are unsatisfactory. Both patients and dentists are confronted by the problem of dental prostheses that do not fit securely, especially in the lower jaw.

This problem has been solved in accordance with German Utility Patent DE-GM No. 8 225 853 with a valve ring groove that extends around the edge of the prosthesis, that surrounds the hollow formed by the prosthesis, and that accepts a soft sealing material that can be tolerated by the tissues. It is practical for the groove to be uniform in depth and to be undercut. It may extend continuously around the total hollow in the prosthesis or be in sections.

An additional problem has, however, been encountered in creating a groove precisely enough to be practical.

SUMMARY OF THE INVENTION

The object of the present invention is to provide a method that makes it possible to precisely create the ring groove in the prosthesis that is necessary to accommodate the soft sealing material. The known method of fraising out a groove has proven to be too imprecise to be practical.

This object is attained in accordance with the invention in that an occlusion model representing a jaw impression obtained with the existing prosthesis is prepared, a guideline is marked a short distance, about 1 mm for example, from the edge of the prosthesis, a thin layer of adhesive is applied to the penciled guideline on the occlusion model to fasten a wax wire along the penciled guideline and both ends of the wire fused together, the dental prosthesis is ground, shortened that is, to a volume at which the wax wire, when it is placed on the occlusion model, will be completely unencumbered with respect to the prosthesis, the edge of the prosthesis is refilled with a mass of plastic until the wax wire is completely embedded in it and the freshly applied mass of plastic polymerized, the prosthesis, which has been removed from the occlusion model is worked and the wax wire baked or evaporated out of it, the ring groove left when the wax wire is removed ground out, and tissue-compatible soft sealing material inserted into the ring groove in the dental prosthesis all the way around.

A preferred embodiment of the invention will now be described with reference to the attached drawings, wherein

BRIEF DESCRIPTION OF THE DRAWINGS

FIG. 5 is a perspective view and shows how the wax wire lies freely in place, while liquid plastic is poured in;

DETAILED DESCRIPTION OF THE PREFERRED EMBODIMENT

Figure 1:
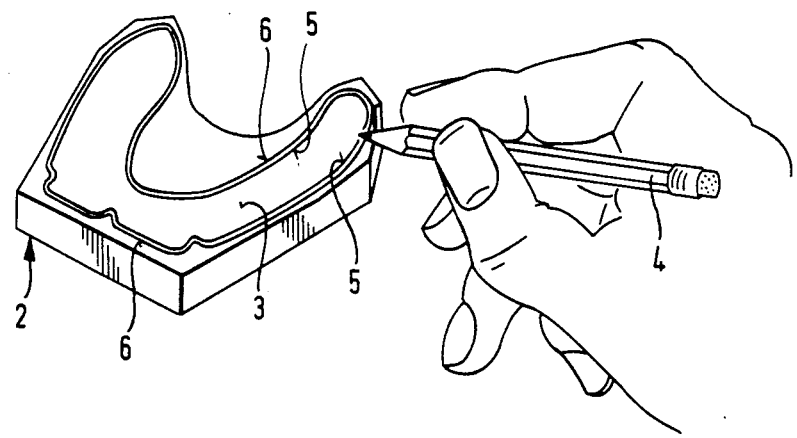
FIG. 1 is a perspective view and shows the step for reproducing the jaw impression of the prosthesis.

FIG. 1 illustrates an occlusion model 2 obtained from an existing dental prosthesis 1 and reproducing the jaw impression 3 of the prosthesis. A guideline 5 is drawn, with a pencil 4 for example, a short distance, about 1 mm for example, from the edge 6 of the prosthesis on occlusion model 2.

Figure 2:
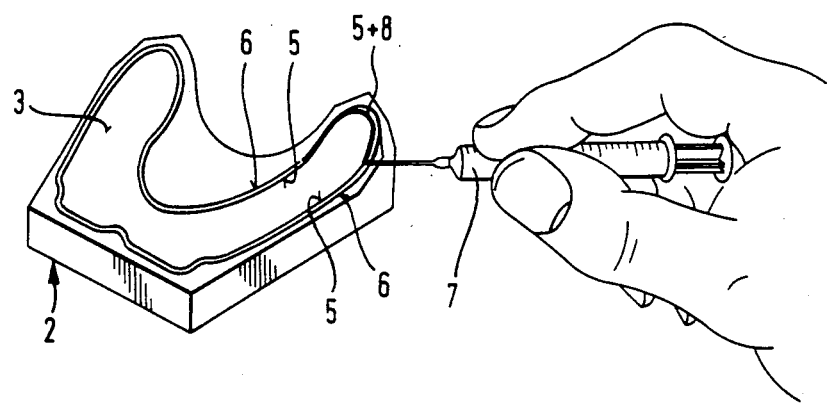
FIG. 2 is a perspective view and shows the step for applying a thin layer of adhesive.
Figure 3:
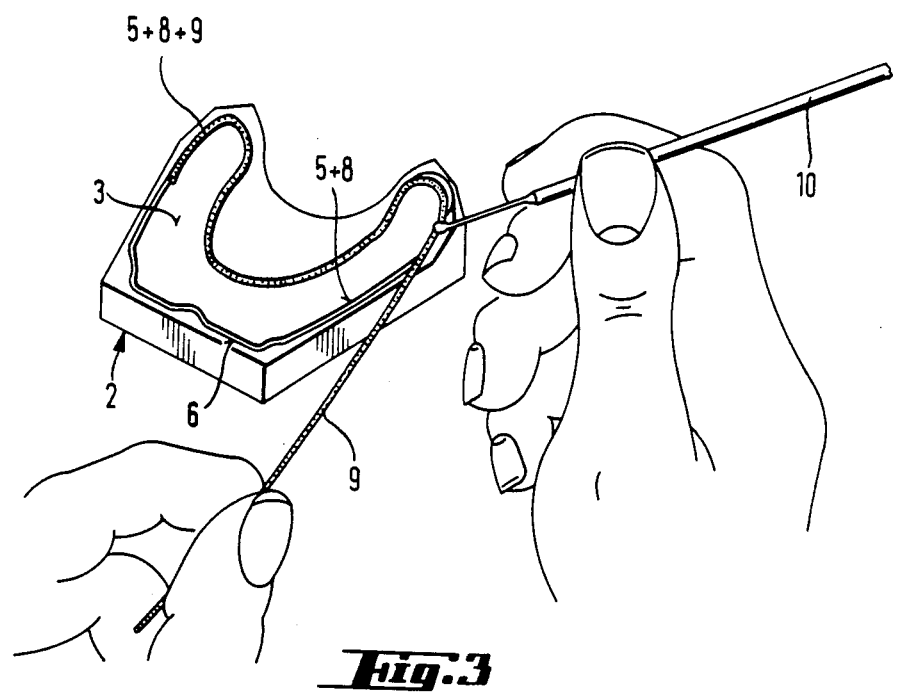
FIG. 3 is a perspective view and shows the step for attaching a wax wire.

A thin layer of adhesive 8 is applied as illustrated in FIG. 2 to the penciled guideline 5 on occlusion model 2 with an adhesive-application syringe 7. Adhesive 8 is intended to fasten a wax wire 9 along penciled guideline 5 as illustrated in FIG. 3. Wax wire 9 is subsequently pressed onto occlusion model 2 with a spatula-like tool 10. Both ends of the wax wire 9 are then fused together on occlusion model 2.

Figure 4:
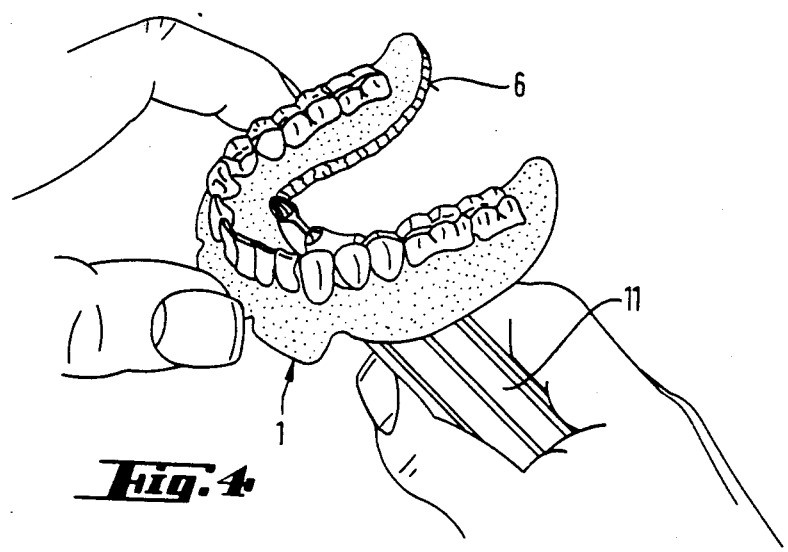
FIG. 4 is a perspective view and shows the step of shortening the prosthesis.

As will be evident from FIG. 4, dental prosthesis 1 is then shortened at its edge 6 with a manual fraise 11 until, when it is placed on occlusion model 2, the wax wire 9 adhering to occlusion model 2 will be completely unencumbered.

Figure 5:
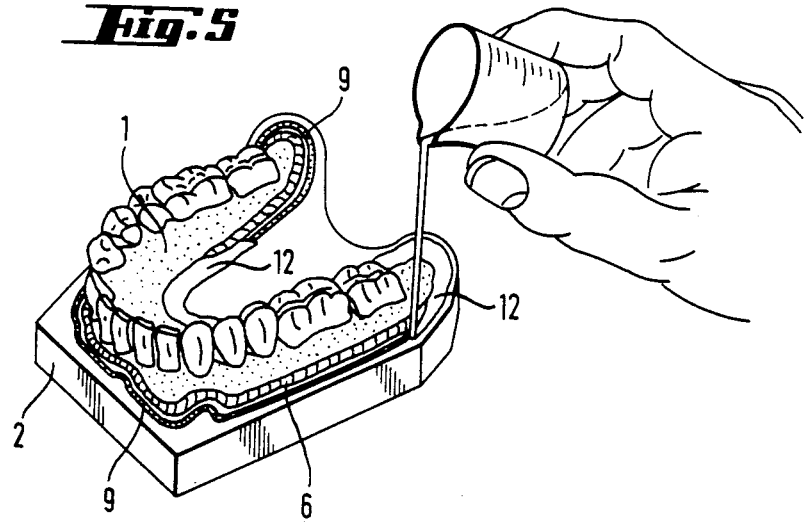

FIG. 5 illustrates how a liquid mass 12 of plastic is poured along the edge 6 of the prosthesis until wax wire 9 is completely embedded in it. The requisite polymerization of the freshly applied mass 12 of plastic is carried out conventionally in a pressurized vessel.

Figure 6:
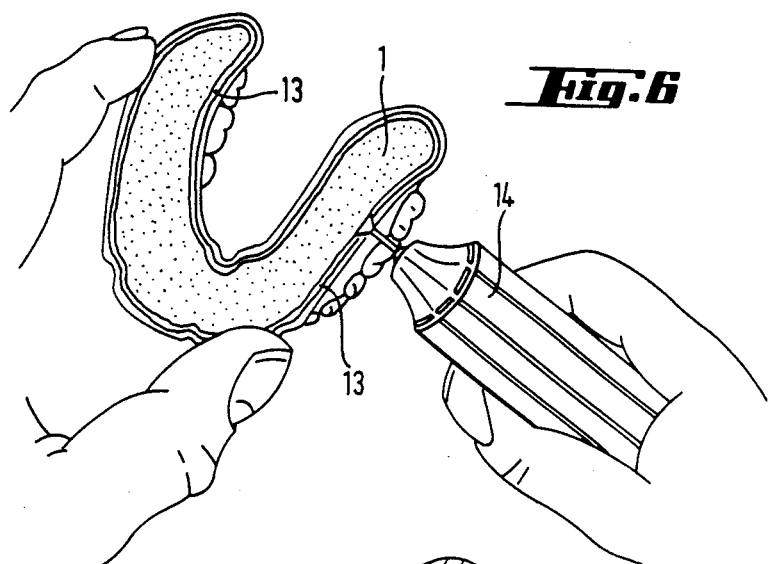
FIG. 6 is a perspective view and shows a polishing step.
Figure 7:
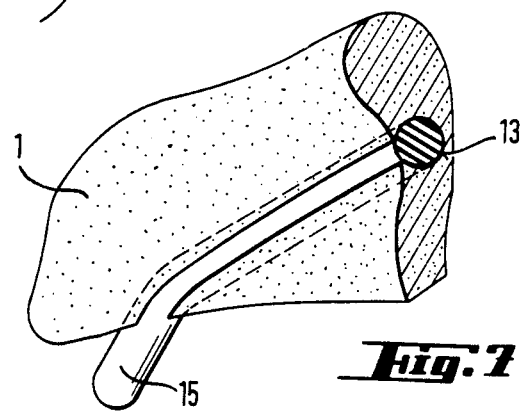
FIG. 7 is a perspective view and shows an insertion step into the prosthesis.

Once dental prosthesis 1, which has been removed along with wax wire 9 from occlusion model 2 has been worked, maintaining a minimal wall thickness, wax wire 9 is baked or evaporated out to remove it cleanly from prosthesis 1. The perfectly matching ring groove 13 left in prosthesis 1 as illustrated in FIG. 6 is ground out with a grinder 14 and the tissue-compatible soft sealing material 15 illustrated in FIG. 7 inserted into the ring groove 13 in dental prosthesis 1 all the way around.

The reliable suction adhesion of dental prosthesis 1 is obtained because soft sealing material 15 has the property of always flowing to wherever suction is weak. It accordingly constantly maintains its effect and the loosening of dental prosthesis 1 is prevented for a long time.

We claim:

1. In a method of making dental prostheses for the upper or lower jaw out of new prostheses produced by conventional means or out of old prostheses provided with a correction impression, comprising the steps of: preparing an occlusion model representing a jaw impression obtained with the existing prosthesis; marking a guideline a substantially short distance from the edge of the prosthesis; applying a thin layer of adhesive to said guideline on the occlusion model to fasten a wax wire along the guideline and both ends of the wire fused together; grinding the dental prosthesis to a volume at which the wax wire when placed on the occlusion model will be completely unencumbered with respect to the prosthesis; refilling the edge of the prosthesis with a mass of plastic until the wax wire is completely embedded in the plastic and the freshly applied mass of plastic is polymerized; working the prosthesis after removal from the occlusion model; baking or evaporating the wax wire out of the prosthesis; grinding out the ring groove left when the wax wire is removed; and inserting tissue-compatible soft sealing material into the ring groove in the dental prosthesis thereabout.

2. A method as defined in claim 1, wherein said guideline is marked 1 mm from the edge of the prosthesis.

3. A method as defined in claim 1, wherein said guideline is marked with a pencil.

4. A method as defined in claim 1, wherein said grinding step shortens said prosthesis.

5. In a method of making dental prostheses for the upper or lower jaw out of new prostheses produced by conventional means or out of old prostheses provided with a correction impression, comprising the steps of: preparing an occlusion model representing a jaw impression obtained with the existing prosthesis; marking a guideline with a pencil substantially 1 mm from the edge of the prosthesis; applying a thin layer of adhesive to said penciled guideline on the occlusion model with a syringe to fasten a wax wire along the penciled guideline and fusing both ends of the wire together; pressing wax wire onto the occlusion model with a spatula-shaped tool grinding the dental prosthesis to a volume at which the wax wire when placed on the occlusion model will be completely unencumbered with respect to the prosthesis, said ginding shortening said prosthesis; refilling the edge of the prosthesis with a liquid mass of plastic until the wax wire is completely embedded in the plastic and the freshly applied mass of plastic is polymerized in a pressurized vessel; working the prosthesis after removal from the occlusion model; baking or evaporating the wax wire out of the prosthesis; grinding out the ring groove left when the wax wire is removed; and inserting tissue-compatible soft sealing material into the ring groove in the dental prosthesis thereabout, substantially reliable suction adhesion of the prosthesis being obtained due to said soft sealing material flowing to wherever suction is weak.

* * * * *